(12) United States Patent
Lee et al.

(10) Patent No.: US 9,842,270 B2
(45) Date of Patent: Dec. 12, 2017

(54) APPARATUS AND METHOD FOR PROVIDING ADDITIONAL INFORMATION FOR EACH REGION OF INTEREST

(71) Applicant: Samsung Electronics Co., Ltd, Suwon-Si (KR)

(72) Inventors: Chon Hee Lee, Nonsan-si (KR); Yeong Kyeong Seong, Yongin-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 14/700,338

(22) Filed: Apr. 30, 2015

(65) Prior Publication Data

US 2015/0317794 A1 Nov. 5, 2015

(30) Foreign Application Priority Data

Apr. 30, 2014 (KR) ........................ 10-2014-0052823

(51) Int. Cl.
| | |
|---|---|
| *G06K 9/00* | (2006.01) |
| *G06K 9/46* | (2006.01) |
| *G06T 7/00* | (2017.01) |
| *A61B 8/08* | (2006.01) |
| *A61B 8/06* | (2006.01) |
| *A61B 8/00* | (2006.01) |

(52) U.S. Cl.
CPC ............. *G06K 9/46* (2013.01); *A61B 8/06* (2013.01); *A61B 8/469* (2013.01); *A61B 8/485* (2013.01); *A61B 8/5246* (2013.01); *A61B 8/5261* (2013.01); *G06T 7/0012* (2013.01); *A61B 8/0825* (2013.01); *A61B 8/4416* (2013.01); *A61B 8/461* (2013.01); *G06T 2207/10081* (2013.01); *G06T 2207/10088* (2013.01); *G06T 2207/10116* (2013.01); *G06T 2207/10132* (2013.01); *G06T 2207/20104* (2013.01)

(58) Field of Classification Search
None
See application file for complete search history.

(56) References Cited

U.S. PATENT DOCUMENTS

| | | | |
|---|---|---|---|
| 9,111,027 B2* | 8/2015 | Kozuka | G06Q 10/06 |
| 9,208,173 B1* | 12/2015 | Doi | G06F 19/321 |
| 9,262,442 B2* | 2/2016 | Doi | G06F 17/30253 |
| 2007/0238951 A1* | 10/2007 | Ferenczi | A61B 5/055 |
| | | | 600/407 |

(Continued)

OTHER PUBLICATIONS

Bernatowicz et al 4D MRI: Future of radiotherapy of moving target? magnetom flash Feb. 2015; www.siemens.com/magnetom-world(2015).*

*Primary Examiner* — Nancy Bitar
(74) *Attorney, Agent, or Firm* — Jefferson IP Law, LLP (57) ABSTRACT

An apparatus and method for providing additional information for region of interest. The apparatus includes a region of interest extractor configured to extract regions of interest from a first medical image and at least one second medical image, a region of interest merger configured to merge a region of interest of the at least one second medical image into the first medical image, an additional information determiner configured to determine additional information required for each region of interest, and an additional information provider configured to provide the determined additional information for the each region of interest.

20 Claims, 9 Drawing Sheets

(56) References Cited

U.S. PATENT DOCUMENTS

| | | | |
|---|---|---|---|
| 2008/0039707 A1* | 2/2008 | Sugiyama | G06F 19/321 |
| | | | 600/407 |
| 2009/0039707 A1* | 2/2009 | Ishizeki | H02J 7/345 |
| | | | 307/66 |
| 2010/0021031 A1 | 1/2010 | Brockway et al. | |
| 2010/0135562 A1 | 6/2010 | Greenberg et al. | |
| 2011/0099032 A1* | 4/2011 | Miyasa | G06F 19/321 |
| | | | 705/3 |
| 2011/0270079 A1* | 11/2011 | Osman | A61B 5/702 |
| | | | 600/421 |
| 2012/0220873 A1* | 8/2012 | Hyun | A61B 8/12 |
| | | | 600/443 |
| 2014/0200433 A1* | 7/2014 | Choi | A61B 5/4887 |
| | | | 600/407 |

* cited by examiner

APPARATUS AND METHOD FOR PROVIDING ADDITIONAL INFORMATION FOR EACH REGION OF INTEREST

CROSS-REFERENCE TO RELATED APPLICATION(S)

This application claims the benefit under 35 U.S.C. §119(a) of Korean Patent Application No. 10-2014-0052823, filed on Apr. 30, 2014, in the Korean Intellectual Property Office, the entire disclosure of which is incorporated herein by reference for all purposes.

BACKGROUND

Field

The following description relates to an apparatus and method for providing additional information for each region of interest.

Description of Related Art

Recently, various medical imaging devices, such as, for example, ultrasonic imaging device, an X-ray imaging device, a magnetic resonance imaging (MRI) device, a computed tomography (CT) device, a positron emission tomography (PET) device, have been used to diagnose diseases.

Sometimes physicians may diagnose diseases using a single-modality images, but in most cases, it is difficult to accurately diagnose diseases using the single-modality images. Accordingly, doctors generally diagnose diseases by integrating different modality images.

In these cases, it takes longer for doctors to diagnose diseases, since they have to read whole modality images by viewing them one after another.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Disclosed is an apparatus and method for providing additional information for each region of interest.

In one general aspect, there is provided an apparatus for providing additional information for regions of interest, the apparatus including a region of interest extractor configured to extract regions of interest from a first medical image and at least one second medical image, a region of interest merger configured to merge a region of interest of the at least one second medical image into the first medical image, an additional information determiner configured to determine additional information required for each region of interest, and an additional information provider configured to provide the determined additional information for the each region of interest.

The at least one second medical image may be an image captured prior to the first image.

The region of interest merger may be further configured to register the first medical image and the at least one second medical image.

The additional information determiner may include a rule storage configured to store at least one rule that defines feature values of regions of interest and additional information required for the feature values, a feature value extractor configured to extract feature values for each of the merged regions of interest, a rule retriever configured to retrieve rules for the extracted feature values from the rule storage, and an additional information selector configured to select additional information for each of the regions of interest based on the retrieved rules.

The additional information comprises new additional information that refers to information associated with examinations to be conducted for an accurate diagnosis, and previous additional information that refers to examination-related information stored in a medical database to be additionally provided for an accurate diagnosis.

The apparatus may include an additional information acquirer configured to acquire additional information required for the each region of interest.

The additional information for the each region of interest may be retrieved from a medical database.

The apparatus may be installed in an ultrasonic imaging device comprising at least two imaging modes selected from a bloodstream imaging mode for obtaining a bloodstream image, an elastography mode for obtaining an elastography image, a general ultrasonic mode for obtaining a general ultrasonic mode, and a high-resolution ultrasonic mode for obtaining a high-resolution ultrasonic image.

The additional information acquirer may be further configured to acquire the additional information for each of the regions of interest by changing an imaging mode of the ultrasonic imaging device based on the determined additional information.

The additional information provider may be further configured to provide a user with additional information acquired for the each region of interest.

The at least one second medical image includes an image of a portion identical to a portion captured by the first image.

The first medical image and the at least one second medical image may be acquired from a medical database.

The feature values may include features of the regions of interest.

The feature value extractor may be further configured to extract the feature values based on analyzing information on each of the merged regions of interest stored in a medical database.

In another general aspect, there is provided a method for providing additional information for region of interest, the method including extracting regions of interest from each of a first medical image and at least one second medical image, merging a region of interest of the at least one second medical image into the first medical image, determining additional information required for each of the merged regions of interest, and providing determined additional information for the each of the regions of interest.

The at least one second medical image may be a medical image captured before the first medical image.

The merging may include registering the first medical image and the at least one second medical image.

The determining may include extracting feature values of each of the merged regions of interest by analyzing information on the merged regions of interest stored in a medical database, retrieving one rule for the extracted feature values from one or more pre-stored rules, and selecting additional information for each of the regions of interest according to the retrieved rule.

The determining may include extracting feature values of each of the merged regions of interest by analyzing information on the merged regions of interest stored in a medical database, retrieving one rule for the extracted feature values from one or more pre-stored rules, and selecting additional information for each of the regions of interest according to the retrieved rule.

The additional information may include new additional information that refers to information associated with examinations to be conducted for an accurate diagnosis, and previous additional information that refers to examination-related information stored in a medical database to be additionally provided for an accurate diagnosis.

The method may include acquiring additional information for the each of the regions of interest based on the determination results.

The acquiring of the additional information may include acquiring additional information for each of the regions of interest from a medical database.

The providing comprises providing a user with the additional information for each of the regions of interest.

Other features and aspects will be apparent from the following detailed description, the drawings, and the claims.

Throughout the drawings and the detailed description, unless otherwise described, the same drawing reference numerals will be understood to refer to the same elements, features, and structures. The drawings may not be to scale, and the relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, apparatuses, and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Figure 1:
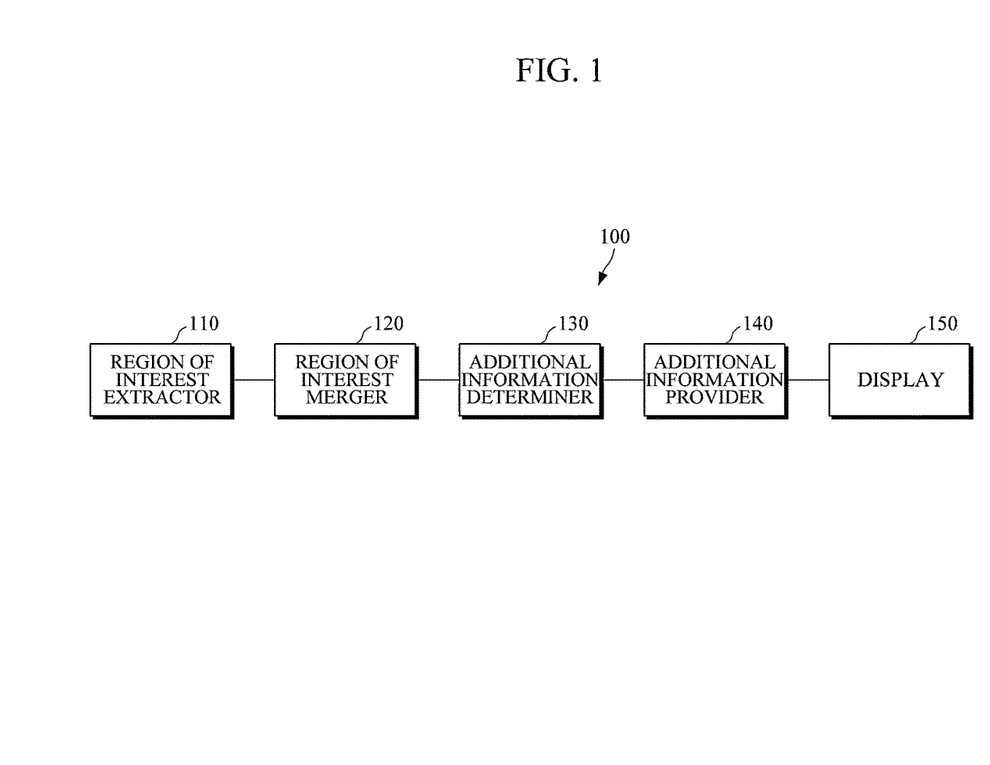
FIG. 1 is a diagram illustrating an example of an apparatus for providing additional information for each region of interest.

FIG. 1 is a diagram illustrating an example of an apparatus for providing additional information for each region of interest. Based on features of each region of interest, an apparatus 100 for providing additional information for each region of interest determines what additional information is needed in medical images for each region of interest to accurately identify each region of interest for diagnosis of diseases, and to provide a user with sufficient information associated with each region of interest. The apparatus 100 for providing additional information for each region of interest may be installed in a medical imaging device.

An example of the apparatus 100 for providing additional information for each region of interest is installed in an ultrasonic imaging device. The ultrasonic imaging device includes various imaging modes, such as, for example, a bloodstream imaging mode for obtaining bloodstream images, an elastography mode for obtaining elastography images, a general ultrasonic mode for obtaining general ultrasonic images, and a high-resolution ultrasonic imaging mode for obtaining high-resolution ultrasonic images. The apparatus 100 for providing additional information for each region of interest may be installed in various other diagnostic imaging devices without departing from the spirit and scope of the illustrative examples described.

Referring to FIG. 1, the apparatus 100 for providing additional information for each region of interest includes a region of interest extractor 110, a region of interest integrator 120, an additional information determiner 130, an additional information provider 140, and a display 150.

The region of interest extractor 110 may extract a region of interest from each of a first medical image and second medical images.

For example, the region of interest extractor 110 may extract a region of interest from a medical image by applying an algorithm for automatically extracting a lesion area. The extracted region of interest may not only include a malignant lesion, but also a lesion area that is ambiguous to be determined as malignant or benign, or a region with a peculiar feature.

Further, the region of interest extractor 110 may extract a region that is marked by a doctor as being a suspected region when analyzing a medical image, i.e., the region of interest extractor 110 may extract a region directly marked by a user as a region of interest.

The first medical image and the second medical image may be medical images obtained using diagnostic imaging devices such as, for example, an X-ray imaging device, an ultrasonic device, an MRI device, a CT device, and a PET device.

The second medical image may be an image of the same portion as a portion captured in the first medical image, and may be an image captured before the first medical image. Further, the second medical image may not necessarily be a modality image identical to the first medical image, and if there is a plurality of second medical images, modalities of those second medical images may be different.

For example, it is assumed that there are three second medical images, in which the first medical image may be an ultrasonic image showing a current state of a patient, and the second medical image may be an X-ray image captured six months earlier, an ultrasonic image captured six months earlier, and an X-ray image captured immediately before the first medical image.

The region of interest merger 120 may register the first medical image and the second medical image, and merge regions of interest of the second medical images into the first medical image. The image registration refers to a process of geometrically registering physically similar regions in two or more different images captured at different angles.

In an embodiment, the region of interest merger 120 merges regions of interest of the second medical images into the first medical image, such that a region of interest that is extracted from the second medical images may be merged into the first medical image.

The additional information determiner 130 may determine what additional information is necessary for each of the merged regions of interest. The additional information refers to examination information or examination-related information needed for accurately identifying regions of interest to diagnose diseases. The additional information may be divided into new additional information and previous additional information.

The new additional information refers to information that is not acquired, collected, or stored in a medical database, such as, for example, an electronic medical record (EMR) and a personal health record (PHR). The new additional information also refers to information associated with examinations that are needed for an accurate diagnosis. The previous additional information refers to examination information or examination-related information that has been acquired, or collected previously by various methods and stored in a medical database. The previous additional information is provided to a user for an accurate diagnosis. The additional information determiner 130 will be further described with reference to FIG. 2.

The additional information provider 140 may provide a user with determination results obtained by the additional information determiner 130. For example, the additional information provider 140 may provide a user the determination results of the additional information determiner 130 through the display 150. The display 150 may display determination results of the additional information determiner 130.

Figure 2:
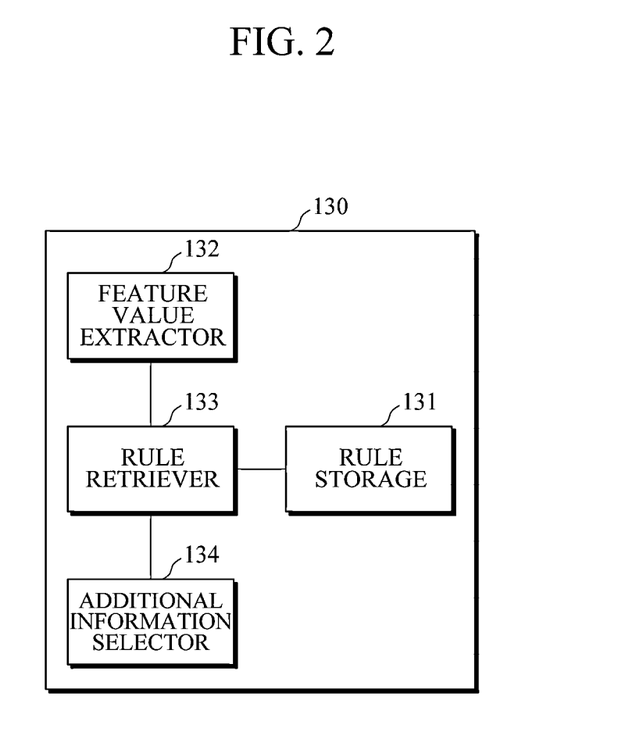
FIG. 2 is a diagram illustrating an example of an additional information determiner 130.

FIG. 2 is a diagram illustrating an example of an additional information determiner 130. Referring to FIG. 2, the additional information determiner 130 includes a rule storage 131, a feature value extractor 132, a rule retriever 133, and an additional information selector 134.

The rule storage 131 may store various rules that define feature values of regions of interest, and additional information needed for the feature values. These rules may be pre-defined by a domain expert for a variety of situations. For example, for a breast cancer diagnosis, rules may be defined as shown in Table 1 below.

TABLE 1

| Rules | Feature values | Additional information |
|---|---|---|
| Rule 1 | Microcalcification | X-ray images for the past one year are needed. |
| Rule 2 | Malignancy of 40% to 60% | Elastography images are needed. |
| . | . | . |
| . | . | . |
| . | . | . |

The feature value extractor 132 may extract feature values by analyzing previous information on each of the merged regions of interest stored in a medical database. The previous information refers to examination information or examination-related information previously obtained by various methods for regions of interest.

Feature values may be features of regions of interest that were initially extracted, such as, for example, shapes, margins, ultrasonic echo patterns of lesions in these regions of interest. The feature values may also be values obtained by calculation of the initially extracted regions of interest. In this case, the feature value may be expressed in numbers or in labels, but is not limited thereto.

The rule retriever 133 may retrieve rules for feature values extracted by the feature value extractor 132 from the rule storage 131.

For example, the feature value extractor 132 extracts feature values "microcalcification" and "malignancy of 50%" from various images in a specific region of interest that have been stored as previous information, the rule retriever 133 retrieves rule 1 for "microcalcification" and rule 2 for "malignancy of 50%" from the rule storage 131 (see Table 1).

The additional information selector 134 may select additional information for each region of interest from the extracted rules.

For example, if the extracted rules are rule 1 and rule 2, the additional information selector 134 may select X-ray images for the past one year and elastography images as additional information needed for a specific region of interest (see Table 1).

Figure 3:
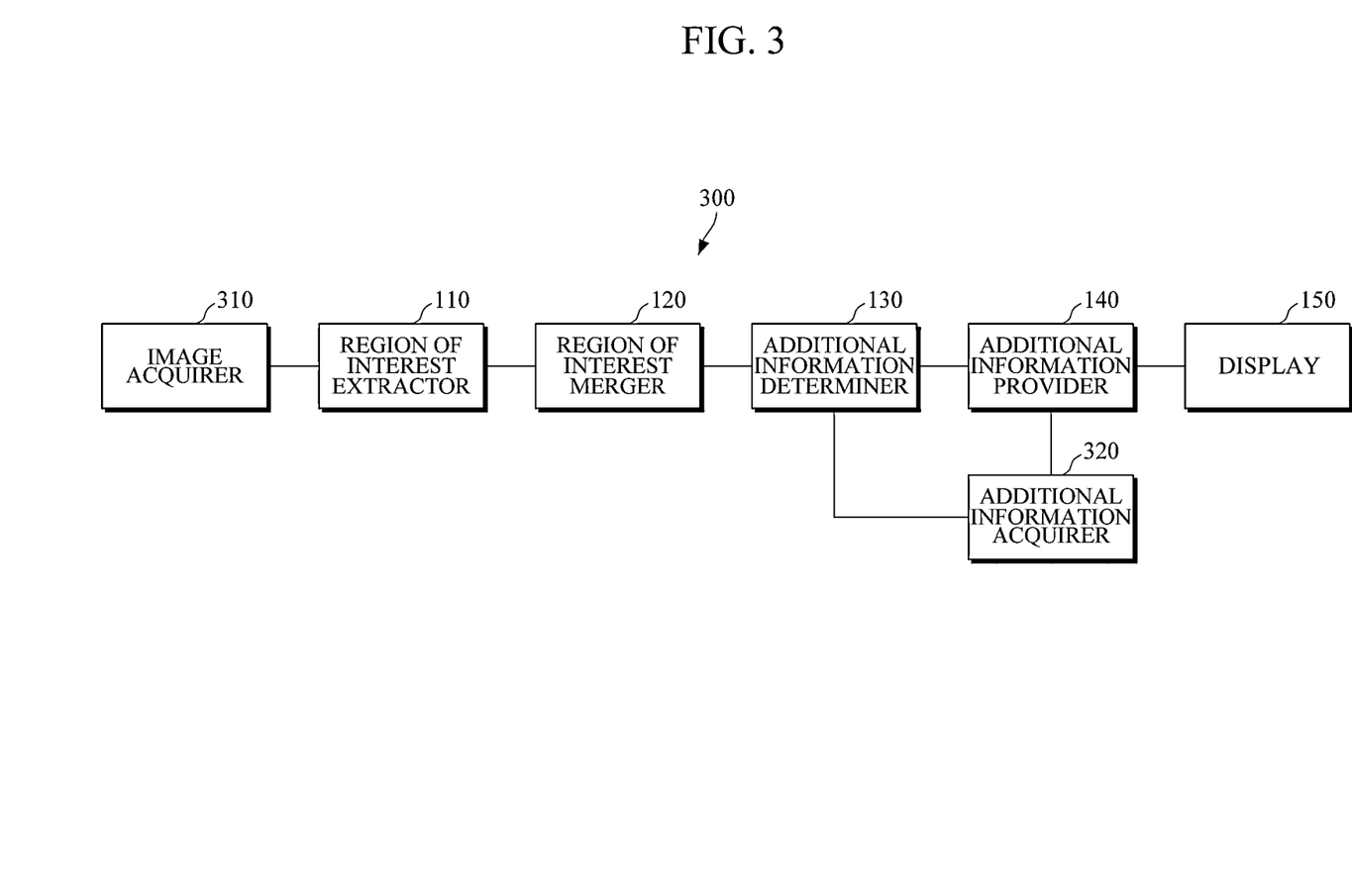
FIG. 3 is a diagram illustrating another example of an apparatus for providing additional information for each region of interest.

FIG. 3 is a diagram illustrating another example of an apparatus for providing additional information for each region of interest.

Referring to FIG. 3, an apparatus 300 for providing additional information for each region of interest may include an image acquirer 310 and an additional information acquirer 320 in addition to the configuration of the apparatus 100 for providing additional information for each region of interest.

The image acquirer 310 may acquire a first medical image and a second medical image. For example, the image acquirer 310 may acquire the first medical image and the second medical image from a medical database. Further, the image acquirer 310 may acquire the first medical image in real time using an ultrasonic imaging device.

The additional information acquirer 320 may acquire additional information determined by the additional information determiner 130 for each region of interest.

If additional information determined by the additional information determiner 130 for a specific region of interest is previous additional information, the additional information acquirer 320 may acquire the additional information by retrieving it from a medical database. For example, if the additional information determiner 130 determines that X-ray images for the past one year are needed for a specific region of interest, the additional information acquirer 320 may retrieve X-ray images captured six months and one week earlier from a medical database for, which are X-ray images for the past one year, among pre-stored existing information.

If additional information determined by the additional information determiner 130 to be required for a specific region of interest is new additional information, the additional information acquirer 320 may acquire the additional information according to a set information acquisition mode. The information acquisition mode may include an automatic acquisition mode that automatically changes an imaging mode of an ultrasonic imaging device to acquire new additional information, and an interactive mode that changes an imaging mode of an ultrasonic imaging device according to a user instruction to acquire new additional information.

As described above, the ultrasonic imaging device includes various imaging modes, such as, for example, a bloodstream imaging mode, an elastography mode, a general ultrasonic mode, and a high-resolution ultrasonic imaging mode, and the additional information determiner 130 determines that bloodstream images are needed as new additional information for a specific region of interest. In the automatic acquisition mode, the additional information acquirer 320 may acquire bloodstream images in the region of interest by automatically changing an imaging mode of an ultrasonic imaging device to a bloodstream imaging mode. In the interactive mode, the additional information provider 140 first transmits a message that a bloodstream image is needed for the region of interest, i.e., a result that has been determined by the additional information determiner 130, to a user through the display 150. Then, if there is an instruction regarding the message, the additional information acquirer 140 changes an imaging mode of an ultrasonic imaging device to a bloodstream imaging mode to acquire a bloodstream image of the region of interest. The additional information provider 140 provides additional information acquired by the additional information acquirer 320 to a user through the display 150.

Figure 4A:
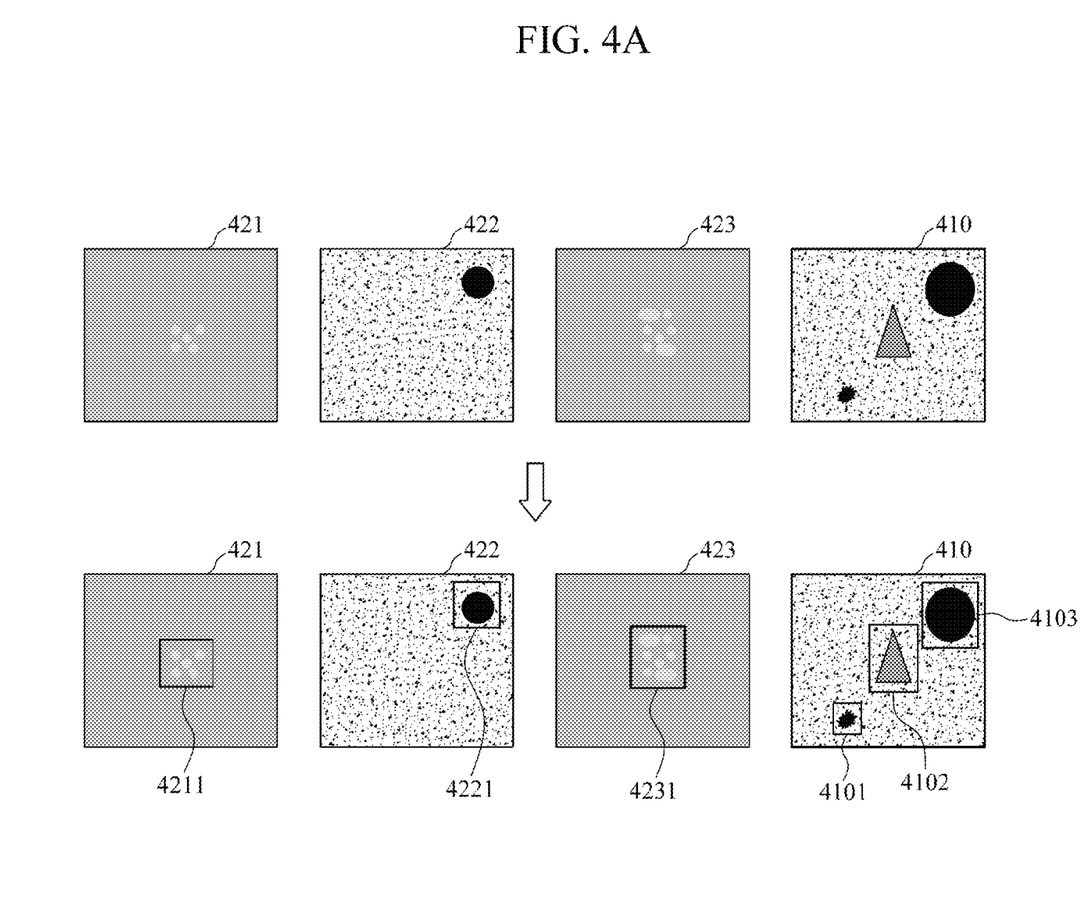
FIG. 4A is a diagram illustrating an example of extracting regions of interest from a first medical image and a second medical image.
Figure 4B:
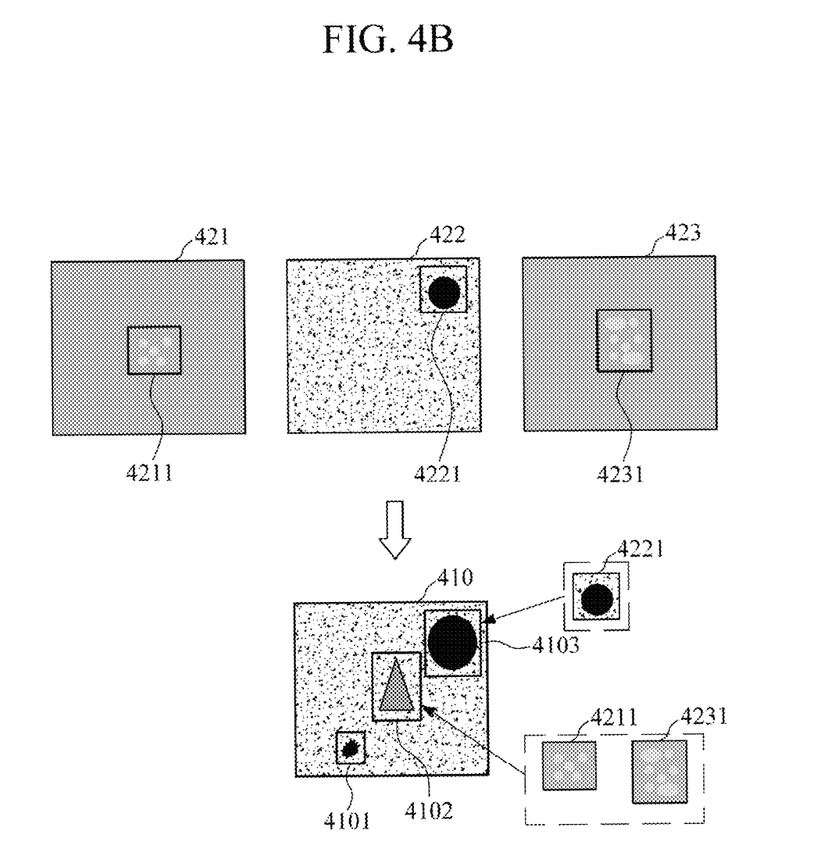
FIG. 4B is a diagram illustrating an example of merging regions of interest of second medical images into a first medical image.
Figure 4C:
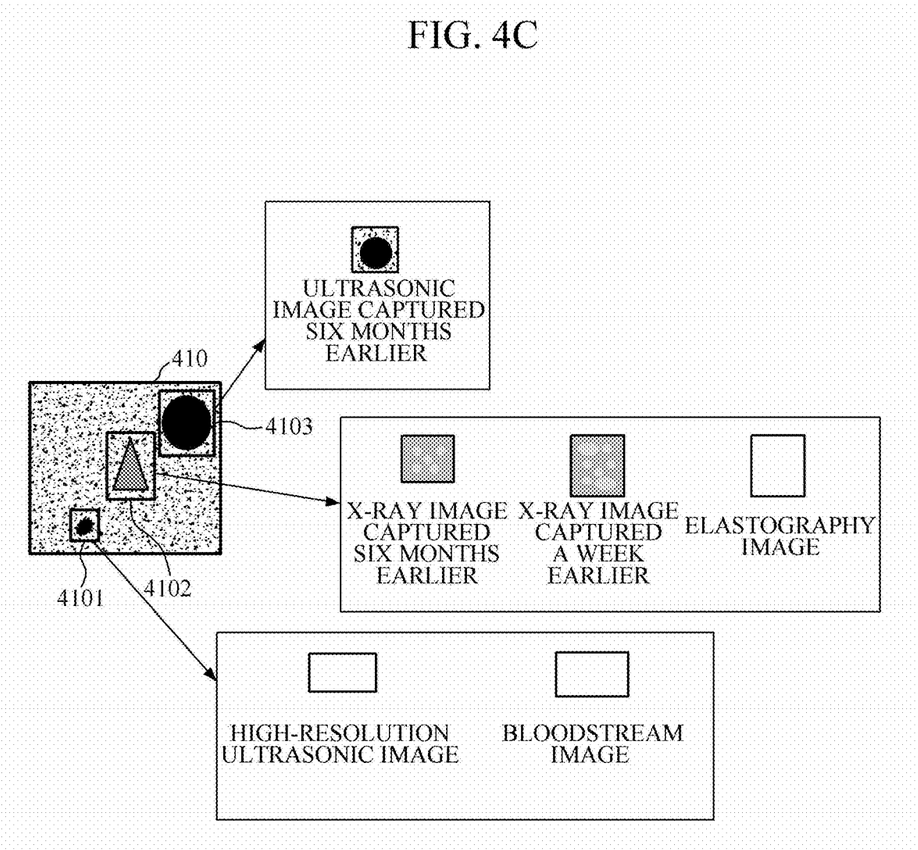
FIG. 4C is a diagram illustrating an example of additional information necessary for each region of interest.

FIGS. 4A to 4C are diagrams illustrating examples of a process of providing additional information for each region of interest. FIG. 4A is a diagram illustrating an example of extracting regions of interest from a first medical image and second medical images. FIG. 4B is a diagram illustrating an example of merging regions of interest of second medical images into a first medical image. FIG. 4C is a diagram illustrating an example of additional information for each region of interest.

Referring to FIG. 4A, a region of interest extractor 110 extracts regions of interest from each of a first medical image 410 and second medical images 421, 422, and 423. As illustrated in FIG. 4A, the first medical image 410 is a current ultrasonic breast image, the second medical image 421 is an X-ray breast image captured six months earlier, the second medical image 422 is an ultrasonic breast image captured six months earlier, and the second medical image 423 is an X-ray breast image captured a week earlier. The region of interest extractor 110 extracts a region of interest 4211 from the second medical image 421, a region of interest 4221 from the second medical image 422, a region of interest 4231 from the second medical image 423, and regions of interest 4101 to 4103 from the first medical image 410.

Referring to FIG. 4B, the region of interest merger 120 registers the first medical image 410 and the second medical images 421 to 423. The region of interest merger 120 merges the regions of interest of the second medical images 421 to 423 into the first medical image 410. As illustrated in FIG. 4B, the region of interest merger 120 merges the region of interest 4211 of the second medical image 421 and the region of interest 4231 of the second medical image 423 into the region of interest 4102 of the first medical image 410. The region of interest merger 120 merges the region of interest 4221 of the second medical image 422 into the region of interest 4103 of the first medical image 410.

Referring to FIG. 4C, the additional information determiner 130 extracts feature values of each of the regions of interest 4101, 4102, and 4103 merged into the first medical image 410, and determines what additional information is needed for each of the regions of interest 4101, 4102, and 4103 based on the extracted feature values and pre-stored rules.

As illustrated in FIG. 4C, the region of interest 4101 is a region of interest that was not extracted from the second medical images 421 to 423 captured before the first medical image 410, and exhibits a small lesion. As the small lesion in the region of interest 4101 is ambiguous to be determined as malignant or benign, the additional information determiner 130 determines that a high-resolution ultrasonic image and a bloodstream image are needed for an accurate diagnosis.

The region of interest 4102 exhibits a feature of microcalcification extracted by analyzing the second medical image 421, which is an X-ray image captured six months earlier, and the second medical image 423, which is an X-ray image captured a week earlier, and a feature of malignancy of 50% extracted by analyzing the first medical image 410. Microcalcification in the region of interest 4102 shows that there is a high possibility of a breast cancer and more careful observation is needed. The determination of the region of interest 4102 as malignant or benign is ambiguous, which does not appear in the second medical image 422, which is an ultrasonic image captured six months earlier, but appears in the first medical image 410, which is a current ultrasonic image. Accordingly, the additional information determiner 130 determines that X-ray images captured six months earlier and a week earlier are needed for an accurate diagnosis and to identify the microcalcification progression. Further, the additional information determiner 130 determines that elastography images are needed, since current information is not sufficient to determine whether the region of interest 4102 is malignant or benign.

The region of interest 4103 exhibits a feature of a benign tumor (e.g., fibroadenoma) based on the analysis of the second medical image 422 that is an ultrasonic image captured six months earlier and the first medical image 410 that is a current ultrasonic image. There is a need to check whether or not the size of such benign tumor has increased, because even if it is not harmful to health, it is better to remove such benign tumor if it increases in size. Accordingly, the additional information determiner 130 determines that an ultrasonic image captured six months earlier is needed for the region of interest 4103.

Figure 5:
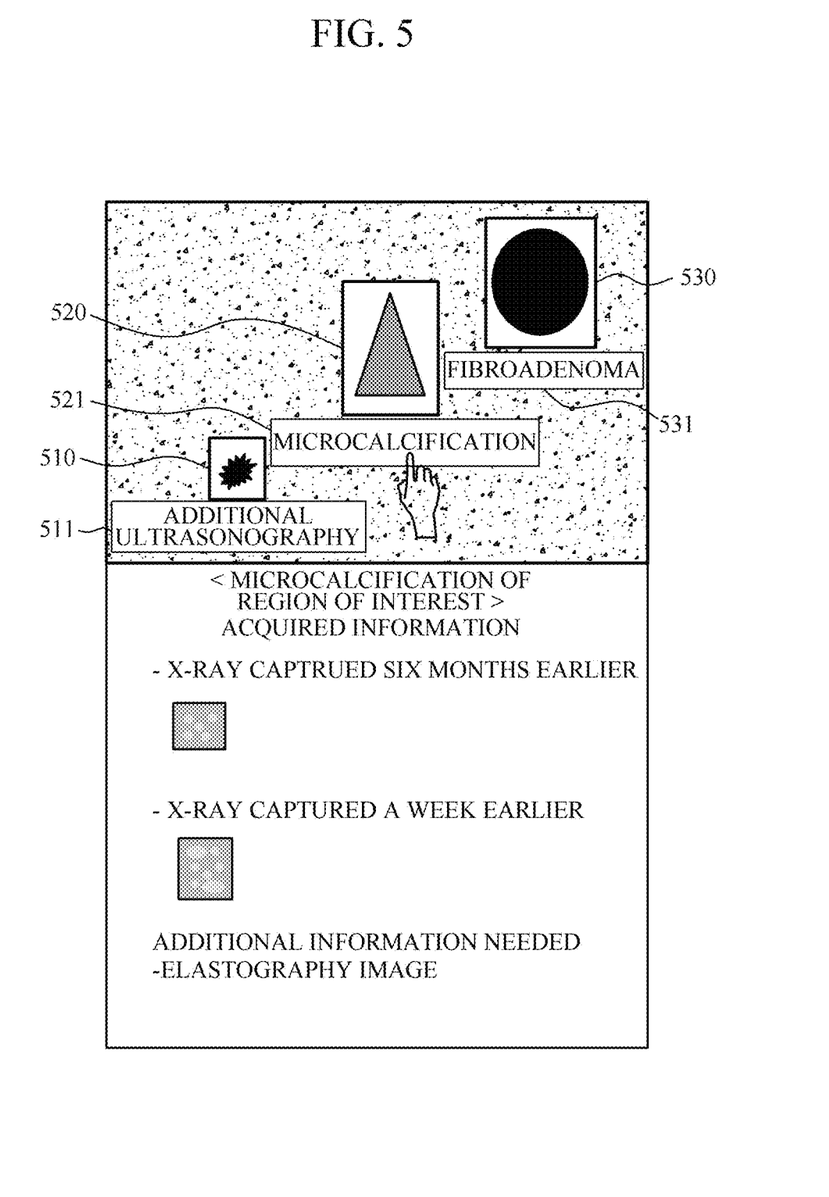
FIG. 5 is a diagram illustrating an example of providing a user with additional information necessary for each region of interest.

FIG. 5 is a diagram illustrating an example of providing a user with additional information necessary for each region of interest.

Referring to FIG. 5, the additional information provider 140 summarizes feature values or additional information for regions of interest 510, 520, and 530 using various summarization methods in short sentences to create snippets 511, 521, and 531. The additional information provider 140 displays the created snippets 511, 521, and 531 as a hyperlink at the bottom of each of the regions of interest 510, 520, and 530. If a user clicks the snippet 521, the additional information provider 140 provides additional information on the region of interest 520 corresponding to the snippet 521 to a user through the display 150.

FIG. 5 illustrate an example in which snippets corresponding to each region of interest are displayed at the bottom thereof, but the position of the snippets is not limited thereto, and the snippets may be displayed anywhere, such as, for example on the left or right, or at the top or bottom of each region of interest, without departing from the spirit and scope of the illustrative examples described.

Figure 6:
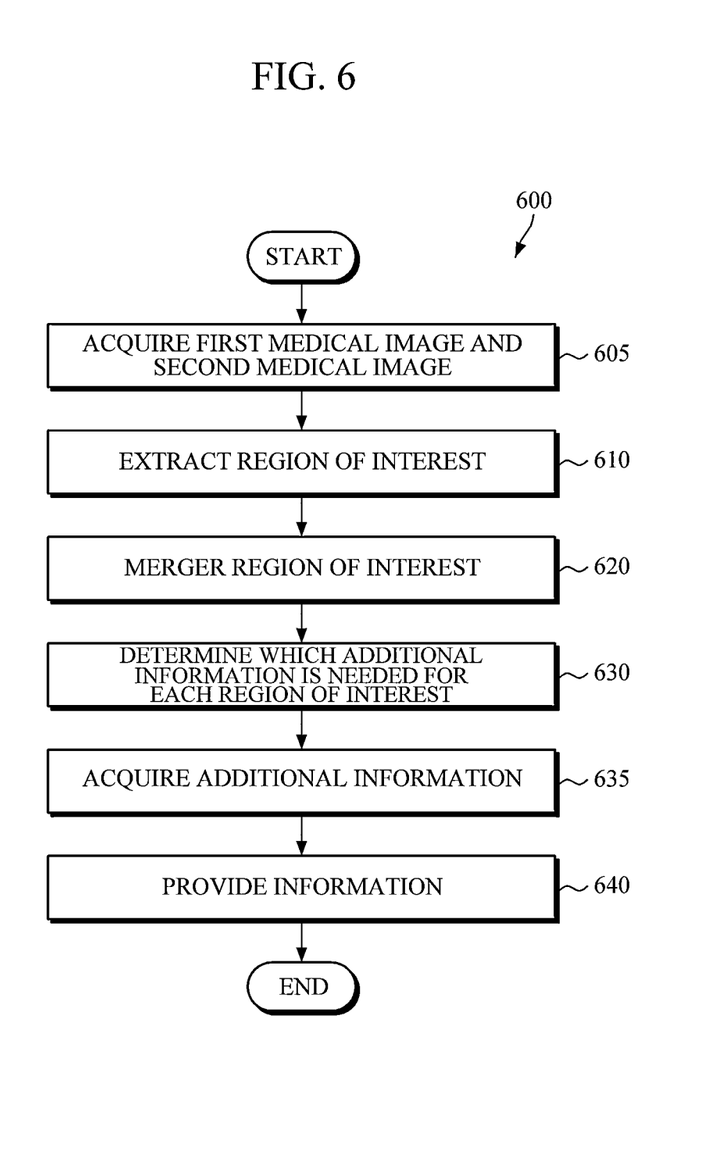
FIG. 6 is a diagram illustrating an example of a method for providing additional information for each region of interest.

FIG. 6 is a diagram illustrating an example of a method for providing additional information for each region of interest. The operations in FIG. 6 may be performed in the sequence and manner as shown, although the order of some operations may be changed or some of the operations omitted without departing from the spirit and scope of the illustrative examples described. Many of the operations shown in FIG. 6 may be performed in parallel or concurrently. The above descriptions of FIGS. 1-5, are also applicable to FIG. 6, and are incorporated herein by reference. Thus, the above description may not be repeated here.

Referring to FIG. 6, a method 600 for providing additional information for each region of interest includes extracting regions of interest (ROI) from each of a first medical image and second medical images in 610. For example, the region of interest extractor 110 may extract regions of interest from medical images using an algorithm for automatically extracting a lesion area, or a user may mark regions in medical images that are to be extracted.

The first medical image and the second medical image may be medical images obtained by using an imaging device, such as, for example, an MRI device, a CT device, a PET device, and an X-ray device.

The second medical image may be an image of the same portion as a portion captured in the first medical image, and may be an image captured before the first image. Further, the second medical image may not necessarily be a modality image identical to the first medical image. If there are a plurality of second medical images, modalities of those second medical images may be different.

In 620, a region of interest of the second medical image is merged into the first medical image. For example, the region of interest merger 120 may register the first medical image and the second medical image, and may merge a region of interest of the second medical image into the first medical image.

In 630, it is determined what additional information is required for each of the merged regions of interest. For example, the additional information determiner 130 may determine what additional information is required for each region of interest based on feature values of each region of interest and pre-stored rules.

The additional information refers to examination information or examination-related information that is required for accurately identifying regions of interest to diagnose diseases. The additional information may be divided into new additional information and previous additional information.

The new additional information refers to information that is not acquired, collected, or stored in a medical database, such as, for example, an electronic medical record (EMR), a personal health record (PHR), and to information on or associated with examinations that are required to be further conducted for an accurate diagnosis. The previous additional information refers to information required to be additionally provided for an accurate diagnosis among examination information or examination-related information that has been acquired or collected previously by various methods and stored in a medical database.

In 640, the determination results obtained in 630 may be provided to a user. For example, the additional information provider 140 may provide determination results obtained by the additional information determiner 130 to a user through the display 150.

According to an embodiment, the method 600 for providing additional information for each region of interest may further include acquiring a first medical image and a second medical image in 605. For example, the image acquirer 310 may acquire a first medical image and a second medical image from a medical database. Further, the image acquirer 310 may acquire a first medical image in real time by using an ultrasonic imaging device that includes the apparatus 300 for providing additional information for each region of interest.

According to another embodiment, the method 600 for providing additional information for each region of interest may further include, in 635, acquiring additional information determined that is to be required in 630.

For example, if additional information determined by the additional information determiner 130 to be required for identifying a specific region of interest is previous additional information, the additional information acquirer 320 may acquire the additional information by retrieving it from a medical database.

Further, if additional information determined by the additional information determiner 130 to be required for identifying a specific region of interest is new additional information, the additional information acquirer 320 may acquire new additional information according to an information acquisition mode. In this case, the information acquisition mode may include an automatic acquisition mode that automatically changes an imaging mode of an ultrasonic imaging device to acquire new additional information, and an interactive mode that changes an imaging mode of an ultrasonic imaging device according to a user instruction to acquire new additional information.

Figure 7:
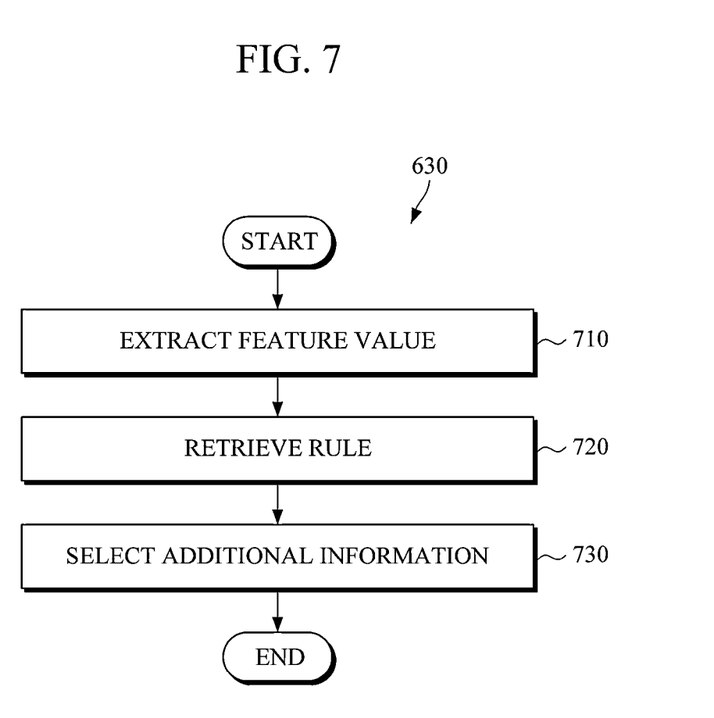
FIG. 7 is a diagram illustrating an example of determining additional information necessary for each region of interest.

FIG. 7 is a diagram illustrating an example of determining additional information necessary for each region of interest. The operations in FIG. 7 may be performed in the sequence and manner as shown, although the order of some operations may be changed or some of the operations omitted without departing from the spirit and scope of the illustrative examples described. Many of the operations shown in FIG. 7 may be performed in parallel or concurrently. The above descriptions of FIGS. 1-6, are also applicable to FIG. 7, and are incorporated herein by reference. Thus, the above description may not be repeated here.

Referring to FIG. 7, determining additional information for each region of interest in 630 may first include analyzing previous information on each of the merged regions of interest stored in a medical database to extract feature values in 710.

In 720, rules for the extracted feature values are retrieved from pre-stored rules.

In 730, additional information required for each region of interest is selected based on the extracted rules.

The apparatuses, components, and units described herein may be implemented using hardware components. The hardware components may include, for example, controllers, sensors, processors, generators, drivers, and other equivalent electronic components. The hardware components may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The hardware components may run an operating system (OS) and one or more software applications that run on the OS. The hardware components also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a hardware component may include multiple processors or a processor and a controller. In addition, different processing configurations are possible, such a parallel processors.

The processes, functions, and methods described above can be written as a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device that is capable of providing instructions or data to or being interpreted by the processing device. The software also may be distributed over network coupled computer systems so that the software is stored and executed in a distributed fashion. In particular, the software and data may be stored by one or more non-transitory computer readable recording mediums. The non-transitory computer readable recording medium may include any data storage device that can store data that can be thereafter read by a computer system or processing device. Examples of the non-transitory computer readable recording medium include read-only memory (ROM), random-access memory (RAM), Compact Disc Read-only Memory (CD-ROMs), magnetic tapes, USBs, floppy disks, hard disks, optical recording media (e.g., CD-ROMs, or DVDs), and PC interfaces (e.g., PCI, PCI-express, Wi-Fi, etc.). In addition, functional programs, codes, and code segments for accomplishing the example disclosed herein can be construed by programmers skilled in the art based on the flow diagrams and block diagrams of the figures and their corresponding descriptions as provided herein.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus for providing additional information for region of interest, the apparatus comprising:
   at least one processor configured to:
      extract at least one region of interest from a first medical image,
      extract at least one region of interest from each of at least one second medical image,
      merge the at least one region of interest extracted from each of the at least one second medical image into the first medical image,
      determine additional information needed for a diagnosis of each of the at least one region of interest merged into the first medical image by retrieving at least one rule for the merged at least one region of interest from at least one pre-stored rule, and selecting the additional information based on the retrieved at least one rule, and
      provide the determined additional information,
   wherein the determined additional information comprises at least one of:
      new additional information that refers to information associated with examinations to be additionally conducted for an accurate diagnosis, or
      previous additional information that refers to examination-related information pre-stored in a medical database to be additionally provided for an accurate diagnosis.

2. The apparatus of claim 1, wherein the at least one second medical image comprises one or more medical images captured prior to the first medical image.

3. The apparatus of claim 1, wherein the at least one processor is further configured to register the first medical image and the at least one second medical image.

4. The apparatus of claim 1, further comprising:
   a memory configured to store at least one rule that defines feature values of regions of interest and at least one additional information required for the feature values.

5. The apparatus of claim 1, wherein the at least one processor is further configured to acquire the determined additional information.

6. The apparatus of claim 1, further comprising: a display configured to display the provided determined additional information.

7. The apparatus of claim 5, wherein the apparatus is configured to be installed in an ultrasonic imaging device comprising at least two imaging modes of:
   a bloodstream imaging mode for obtaining a bloodstream image,
   an elastography mode for obtaining an elastography image,
   a general ultrasonic mode for obtaining a general ultrasonic mode, or
   a high-resolution ultrasonic mode for obtaining a high-resolution ultrasonic image.

8. The apparatus of claim 7, wherein the at least one processor is further configured to acquire the determined additional information for each of the at least one region of interest by changing an imaging mode of the ultrasonic imaging device based on the determined additional information.

9. The apparatus of claim 5, wherein the at least one processor is further configured to provide a user with the acquired determined additional information.

10. The apparatus of claim 1, wherein the at least one second medical image comprises one or more images of a portion identical to a portion captured by the first medical image.

11. The apparatus of claim 1, wherein the first medical image and the at least one second medical image are acquired from a medical database.

12. The apparatus of claim 4, wherein the at least one processor is further configured to:
   extract at least one feature value, from among the feature values, for the merged at least one region of interest, and
   retrieve the at least one rule from the stored at least one rule based on the extracted at least one feature value.

13. The apparatus of claim 12, wherein the at least one processor is further configured to extract the at least one feature value based on analyzing information, stored in a medical database, of the each of the merged at least one region of interest.

14. A method for providing additional information for region of interest, the method comprising:
    extracting at least one region of interest from a first medical image;
    extracting at least one region of interest from each of at least one second medical image;
    merging the at least one region of interest extracted from the at least one second medical image into the first medical image;
    determining additional information needed for a diagnosis of each of the at least one region of interest merged into the first medical image; and
    providing, via a user interface, the determined additional information,
    wherein the determined additional information comprises at least one of:
        new additional information that refers to information associated with examinations to be additionally conducted for an accurate diagnosis, or
        previous additional information that refers to examination-related information pre-stored in a medical database to be additionally provided for an accurate diagnosis,
    wherein the determining of the additional information comprises:
        retrieving at least one rule for the merged at least one region of interest from among one or more pre-stored rules, and
        selecting the additional information according to the retrieved at least one rule.

15. The method of claim 14, wherein the at least one second medical image comprises a medical image captured before the first medical image.

16. The method of claim 14, wherein the merging of the at least one region of interest extracted from the at least one second medical image into the first medical image comprises registering the first medical image and the at least one second medical image.

17. The method of claim 14, wherein the retrieving at least one rule comprises:
    extracting at least one feature value of each of the merged at least one region of interest by analyzing information, stored in a medical database, on each of the merged at least one region of interest, and
    retrieving the at least one rule from among the one or more pre-stored rules based on the extracted at least one feature value.

18. The method of claim 14, further comprising:
    acquiring the determined additional information for the each of the merged at least one region of interest.

19. The method of claim 18, wherein the acquiring of the determined additional information for the each of the merged at least one region of interest comprises acquiring the determined additional information for the each of the merged at least one region of interest from a medical database.

20. A non-transitory computer-readable recording medium having recorded thereon at least one program comprising commands, which when executed by a computer, performs a method, the method comprising:
    extracting at least one region of interest from a first medical image;
    extracting at least one region of interest from each of at least one second medical image;
    merging the at least one region of interest extracted from the at least one second medical image into the first medical image;
    determining additional information needed for a diagnosis of each of the at least region of interest merged into the first medical image; and
    providing, via a user interface, the determined additional information,
    wherein the determined additional information comprises at least one of:
        new additional information that refers to information associated with examinations to be additionally conducted for an accurate diagnosis, or
        previous additional information that refers to examination-related information pre-stored in a medical database to be additionally provided for an accurate diagnosis,
    wherein the determining of the additional information comprises:
        retrieving at least one rule for the merged at least one region of interest from among one or more pre-stored rules, and
        selecting the additional information according to the retrieved at least one rule.

* * * * *